US006960171B2

(12) United States Patent
Sanders

(10) Patent No.: US 6,960,171 B2
(45) Date of Patent: Nov. 1, 2005

(54) INFANT EYE TRAINER

(76) Inventor: David M. Sanders, 5601 Woodrow Ave., Austin, TX (US) 78756

( * ) Notice: Subject to any disclaimer, the term of this patent is extended or adjusted under 35 U.S.C. 154(b) by 132 days.

(21) Appl. No.: 10/730,083

(22) Filed: Dec. 9, 2003

(65) Prior Publication Data

US 2004/0233386 A1 Nov. 25, 2004

Related U.S. Application Data

(60) Provisional application No. 60/471,330, filed on May 19, 2003.

(51) Int. Cl.[7] .......................... A61B 13/00; A61B 3/00
(52) U.S. Cl. ...................... 600/558; 351/203; 248/102; 446/227; 215/11.6
(58) Field of Search . 600/558; 351/203; 248/102–106, 248/918; 446/227, 73, 78; 215/11.1–11.6, 215/387, 395, 400

(56) References Cited

U.S. PATENT DOCUMENTS 3,514,887 A * 6/1970 Jacob .......................... 40/324
4,402,580 A * 9/1983 Ross .......................... 351/203
4,655,715 A * 4/1987 Van de Carr et al. ....... 434/258
5,880,811 A 3/1999 Parisi
6,158,870 A * 12/2000 Ramirez ..................... 362/101
6,379,018 B1 * 4/2002 Rycroft et al. .............. 362/101
6,666,417 B1 * 12/2003 Wright ....................... 248/103
6,750,943 B2 * 6/2004 Pearlman et al. ........... 352/101
6,827,317 B1 * 12/2004 Maki Risaliti .............. 248/102
2003/0112847 A1 * 6/2003 Hsiao ......................... 374/150

* cited by examiner

*Primary Examiner*—Charles Marmor
(74) *Attorney, Agent, or Firm*—Richard C. Litman

(57) ABSTRACT

The infant eye trainer is a device that is mountable on a baby bottle for strengthening and developing infant eyesight. The device utilizes interchangeable media producing an image on a display, which may be viewed by the infant while drinking from the bottle. A variety of images designed to improve, strengthen, and facilitate infant eyesight development, both physically and cognitively are selected for display. The device mounts onto the end of a baby bottle, thus placing it within an infant's focal range. The device may also utilize audiovisual stimuli to further develop infant eyesight and cognition.

17 Claims, 7 Drawing Sheets

INFANT EYE TRAINER

CROSS-REFERENCE TO RELATED APPLICATION

This application claims the benefit of U.S. Provisional Patent Application Ser. No. 60/471,330, filed May 19, 2003.

BACKGROUND OF THE INVENTION

1. Field of the Invention

The present invention relates to eye trainers, and more specifically to an infant eye-training device used in conjunction with a baby bottle.

2. Description of the Related Art

Infants are born with very poor eyesight, possessing about one-fortieth the visual ability of normal adults. Eyesight does not develop naturally. Studies have shown that visual stimulation is necessary to develop good eyesight. The crucial period of eyesight development in infants is within the first six months after birth. During this period, the eye muscles strengthen, thus developing greater focus, and the cones develop, improving color vision.

It is now recognized that parents can help strengthen their infant's eyesight by providing visual stimulation. Nursery decorations, patterned mobiles, and changes of scenery all help to this end. Studies have shown that certain patterns and color combinations, such as high-contrast images, may be more effective than others in strengthening an infant's eyesight at a given stage of eyesight development.

Not only does visual stimulation strengthen infant eyesight, it also leads to cognitive development; the infant begins to understand what it sees. Infants need to develop crucial object perception skills to recognize shape, size, color, orientation, motion, and depth. As an infant develops cognitively, it begins to process these visual clues to develop unit formation and surface segregation skills. Later on in development, infants start to process visual clues to recognize and remember arbitrary relations.

Although sight alone can develop these skills, studies suggest that multimode stimulation enhances an infant's cognitive development. For example, a 1-month-old infant can visually recognize an object's smooth or nubby texture after mouthing the object. Similarly, by three weeks of age, infants can detect the relationship between the sight and sound of an object's impact, and by three to five months of age, infants detect intermodal audiovisual relations in the changing distance, substance, rhythm, and tempo of an event. Additionally, studies have shown that when information is presented concurrently in two sense modalities, such as sight and sound, it selectively recruits the infant's attention and facilitates cognitive development.

Certain properties of objects and events are modality specific. For example, the color and brightness of an object can only be detected visually, while pitch and timber can only be detected aurally. Such properties are called modal properties, whereas properties that can be detected in more than one of the sense modalities are amodal properties.

Often, an event conveys information about an object's properties both modally and amodally. For example, the rhythm of a bouncing ball can be perceived through sight or sound, but the color of the ball can only be visually perceived. There is no correlation between the rhythm of a bouncing ball and its color. Instead the relationship is arbitrary. Relations between properties in two sense modalities that do not predictably occur together in nature or across contexts are called arbitrary intermodal relations. Such relations are best learned intermodally.

Although there are a variety of eye training devices, very few, if any, are designed to be used on infants to develop and strengthen eyesight either physically or cognitively. One factor that may contribute to the lack of infant eye training devices is that only recently scientist and researchers have begun to understand how infant sight develops both physically and cognitively. Another factor is the difficulty of placing such a device where an infant may focus on it, and selectively recruit the infant's attention for any extended period of time.

During the first six months after birth, an infant can focus on objects that are six to fifteen inches away. Therefore, an infant eye-training device should be placed at a distance where the infant can focus on the device. Placing a device on the end of a baby bottle would place it in this focal range.

U.S. Pat. No. 5,880,811, issued to Parisi, discloses a device comprising a visually stimulating ornament having a flat head (2-dimensional) shape that is generally round and attaches to and extends from a baby bottle. The Parisi device is designed to prevent an infant from going cross-eyed by giving it something to focus on with its eyes other than the bottle. Although the invention is referred to as an infant eye trainer, it serves as a prophylaxis in trying to prevent an infant from going cross-eyed. There are no devices, however, that attach to a baby bottle and proactively strengthen and enhance infant eyesight physically or cognitively. A device, which attaches to a baby bottle and that proactively helps to strengthen and develop an infant's eyesight, both physically and cognitively, would be desirable.

None of the above inventions and patents, taken either singly or in combination, is seen to describe the instant invention as claimed.

SUMMARY OF THE INVENTION

The present invention is an infant eye trainer that is mounted on a baby bottle for strengthening and developing infant eyesight. The trainer has a case having a front panel that has a display area for viewing images. The case has a flange extending from the front panel that defines a well adapted for receiving the bottom of a baby bottle. A resilient adapter is placed around the baby bottle and wedged between the bottle and the flange to retain the case on the bottle with the display in the infant's focal area. The images may be provided by transparencies viewed through a transparency viewer, or by images stored on a fixed database and displayed on an LCD display.

Accordingly, it is a principal object of the invention to provide an infant eye training device used in conjunction with a baby bottle to strengthen infant eyesight.

It is another object of the invention to provide an infant eye-training device that will accelerate the development of infant eyesight.

It is a further object of the invention to provide an infant eye-training device that enhances infant cognitive development associated with vision in order to help infants to recognize and remember what they are seeing.

Still another object of the invention is to enhance infant vision through audiovisual stimulation.

Yet another object of the invention is to provide an infant eye-training device that can use different audio and visual programs geared towards the infant's particular developmental stage.

It is an object of the invention to provide improved elements and arrangements thereof in an apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
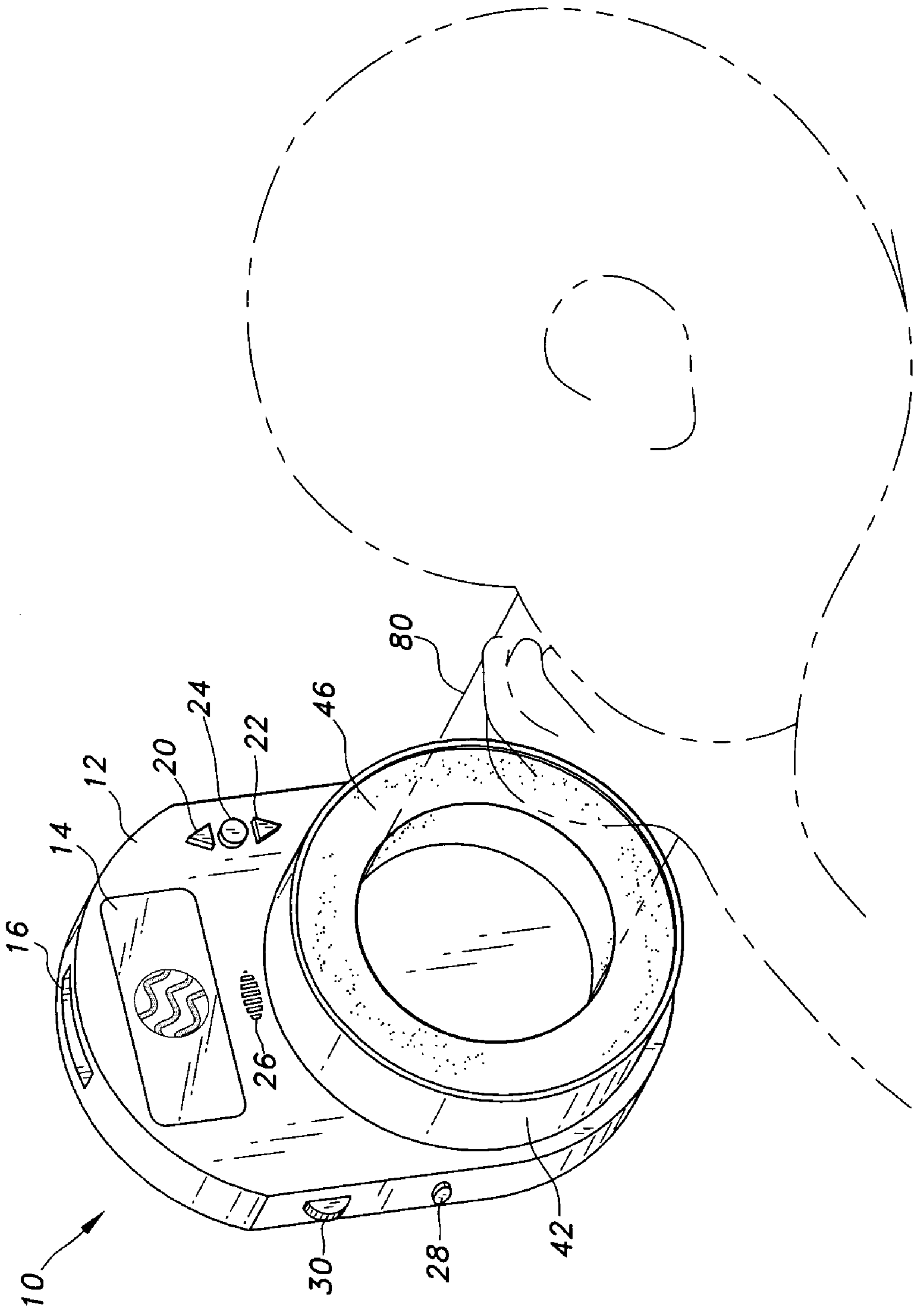
FIG. 1 is an environmental, perspective view of an infant eye trainer according to the present invention.
Figure 2:
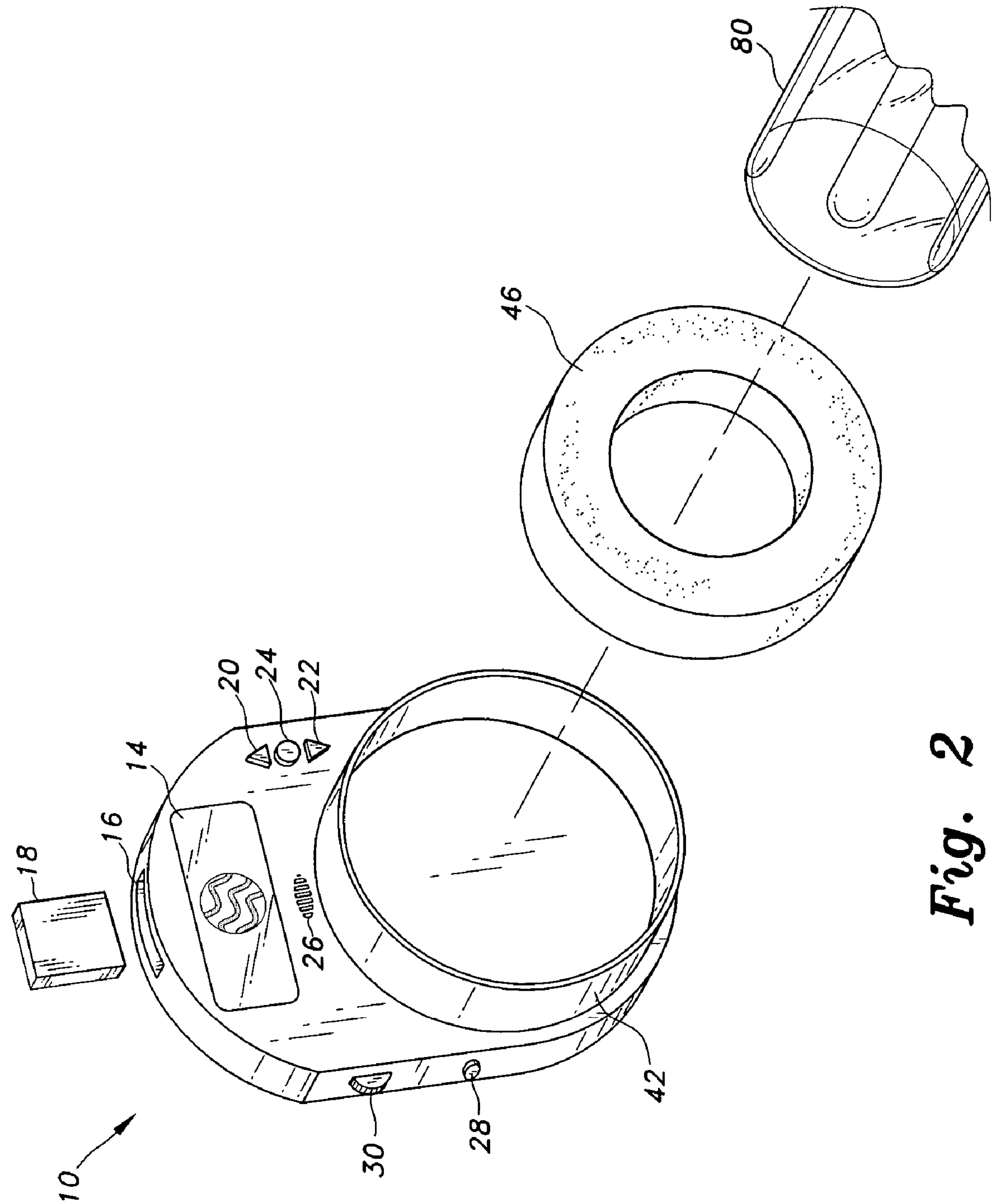
FIG. 2 is an exploded view an infant eye trainer according to the present invention.

FIG. 1 is an environmental, perspective view of an infant eye trainer 10 according to the present invention mounted on a baby bottle 80. The infant eye trainer 10 includes a case 12 that houses electronic components. Embedded in the case is a liquid crystal display (LCD) panel 14. An insertion port 16 is formed in the case 12. As shown in FIG. 2, an external fixed database 18 is inserted into the insertion port 16 to change the image shown on the LCD panel 14. The fixed database is preferably an external read only memory (ROM) cartridge. The fixed database may use any form of memory database, such as memory chips, and the database used will depend on the amount of memory needed to deliver the desired information to the LCD panel 14. Although the insertion port 16 is shown on the upper surface of case 12, it will be obvious to one skilled in the art that the location of the insertion port 16 is not critical, and that the insertion port 16 may be located in any convenient alternative position. A menu toggle up push button 20, a menu toggle down push button 22, and a menu select push button 24 are disposed on the front panel of the case 12. These buttons allow the user to select and implement various setting and options.

The infant eye trainer 10 also has a speaker 26 on the front panel of the case 12. The case 12 is additionally provided with an on/off switch 28, and a volume adjustment 30.

An external read only memory (ROM) 18*a*, in which is stored an infant eye-training program, is incorporated in the external fixed database 18. When the external fixed database 18 is loaded in the infant eye trainer 10, the infant vision-training program is executed in such a way that an image is displayed on the LCD panel 14, and sound is generated by the speaker 26. The fixed database 18 may optionally include music that can be played through the speaker 26. The image may be a still image, or may be a moving image. It will be understood that the provision for audio playback is an optional feature of the infant eye trainer 10, and not essential to the invention.

A flange 42 protrudes from the front surface of case 12. The flange 42 has an inner diameter greater than the diameter of a baby bottle 80, and a depth sufficient to secure the infant eye trainer 10 onto the baby bottle 80. A resilient adapter ring 46 is placed around the base of the baby bottle 80. The infant eye trainer 10 is mounted on the baby bottle 80 by compressing the adapter ring 46 and wedging the ring 46 in the cylindrical well defined by the flange 42 and the front panel of the case 12. The adapter ring 46 may be made from foam rubber or similar material.

Referring to FIG. 2, the adapter ring 46 may be easily removed from the flange 42, and from the baby bottle 80. Thus, the adapter ring 46 may be easily washed or replaced. Because baby bottles do not come in just one shape or size, the inner wall of the adapter ring 46 need not be limited to the shape of a circle, but may be of any shape that will provide sufficient frictional force to secure a baby bottle.

Figure 3:
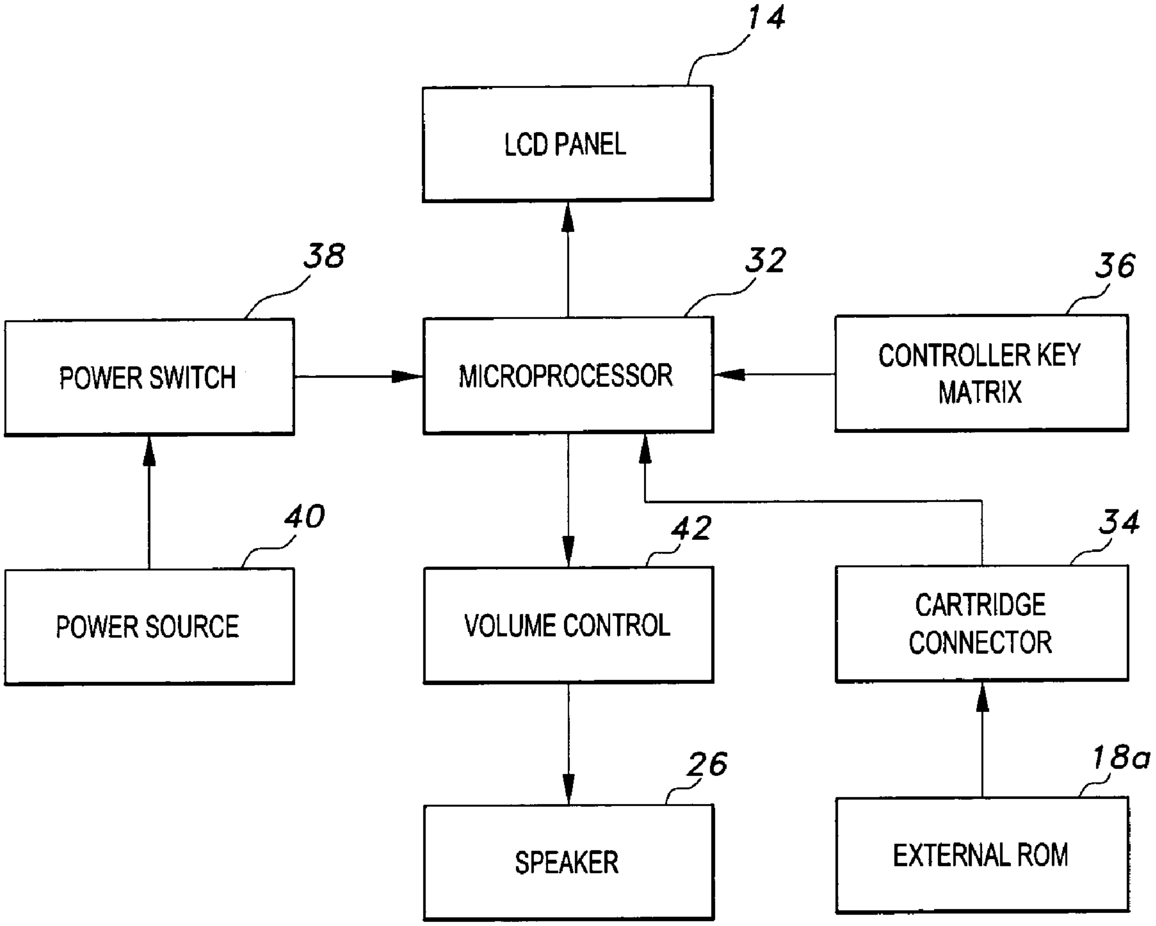
FIG. 3 is a block diagram of an infant eye trainer according to the present invention.

FIG. 3 is a block diagram showing the configuration of the electronic components of the FIG. 1 embodiment. A microprocessor 32 receives input from a cartridge connector 34 and a controller key matrix 36. The microprocessor 32 outputs data to form images on the LCD panel 14, and to produce sound through the speaker 26 when the trainer 10 is so equipped. A power switch 38 switches on and off the current flowing from a power source 40 to the microprocessor 32. A volume control 42 adjusts the sound intensity coming from the speaker 26.

Figure 4:
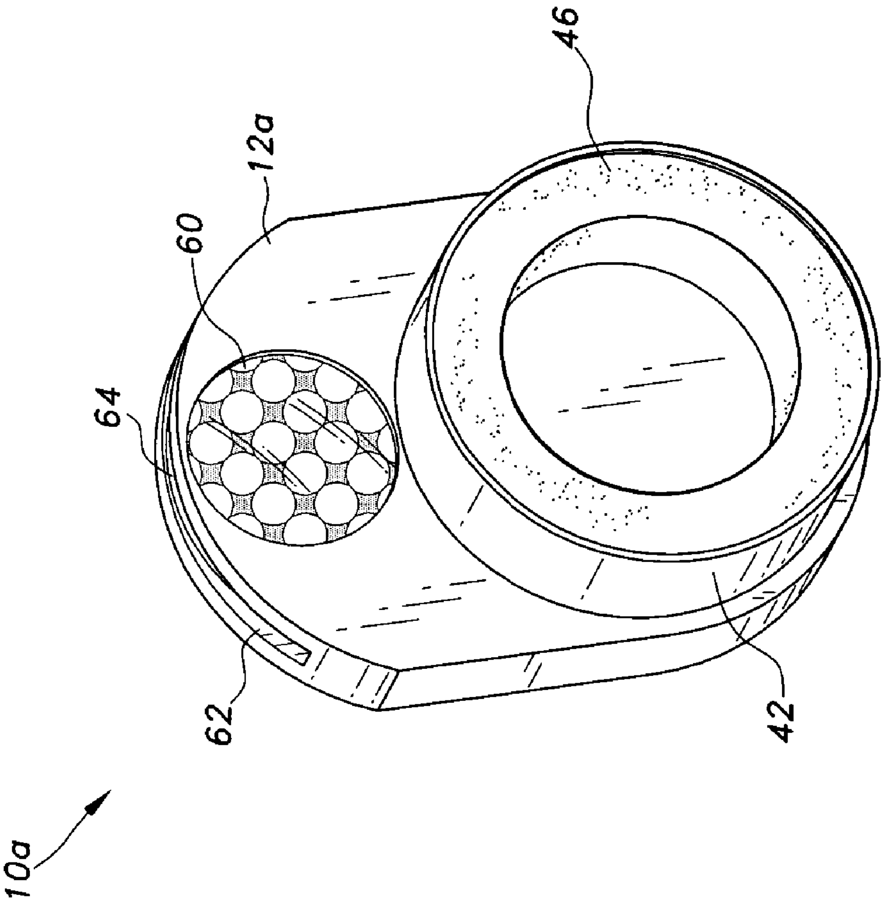
FIG. 4 is a perspective view of an infant eye trainer according to another embodiment of the present invention.

FIG. 4 is a perspective view of an infant eye trainer 10*a* according to another embodiment of the present invention. The infant eye trainer 10*a* includes a case 12*a*. Embedded in the case 12*a* is a viewing window 60, which is translucent or transparent. The viewing window 60 may also be a magnifying lens.

Figure 6:
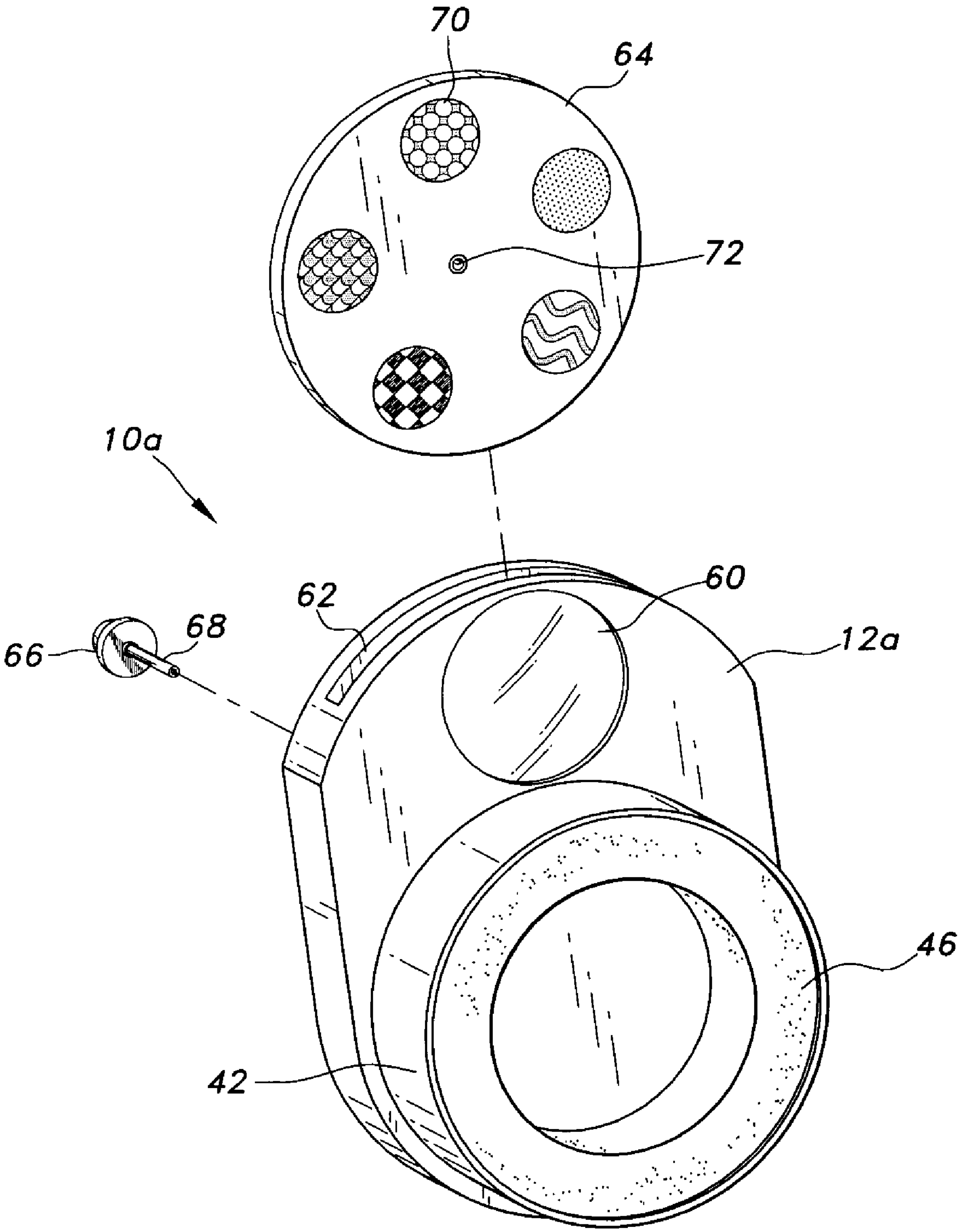
FIG. 6 is an exploded view of the infant eye trainer of FIG. 4.

Referring to FIG. 6, on the upper side surface of case 12*a* an image wheel insertion slit 62 is formed at a position opposite the viewing window 60. An image wheel 64 having at least one translucent image 70 located therein is removably inserted into the image wheel insertion slit 62. It is understood that the image 70 is exemplary in nature, and that there are many different images that may be used to help train infant eyesight.

Figure 5:
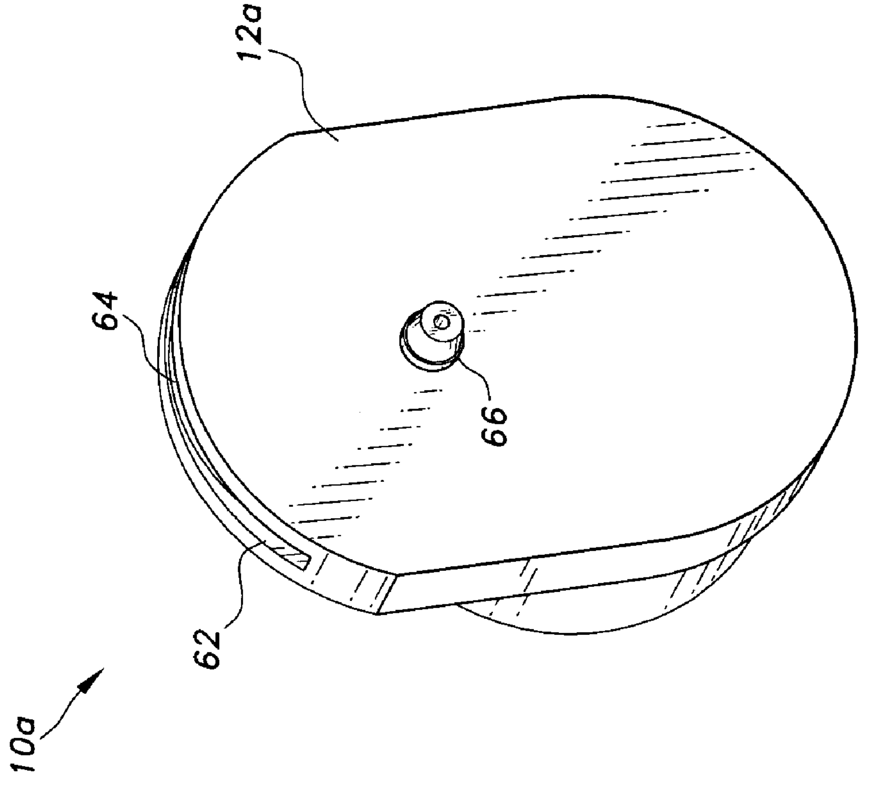
FIG. 5 is a rear view of the infant eye trainer of FIG. 4.

The image wheel 64 may be rotated so as to allow viewing of different images through viewing window 60. A knob 66 is positioned on the rear surface of the case 12, opposite the image wheel insertion slit 62, as seen in FIG. 5. The knob 66 is attached to an axle 68 that is slidably positioned so that the axle 68 may be removably inserted into ring 72. When the axle 68 is positioned within ring 72, rotation of the knob 66 rotates the axle 68, which in turn rotates the image wheel 64. It will be obvious to those in the art that a variety of means may be used to rotate the image wheel 64, such as physically rotating the image wheel 62 with one's hand or finger. Additionally, a wind-up mechanical device may be used to rotate the image wheel 64.

The infant eye trainer 10 may also provide a releasable fastener on the back of the case 12. The releaseable fastener is preferably a Velcro strap but may also be any snap or latch fastener. The Velcro strap will allow the infant eye trainer to be releasably secured to a baby stroller or a crib so that the infant may view the images from the infant eye trainer 10 at times other than when the infant is using a bottle.

Figure 7:
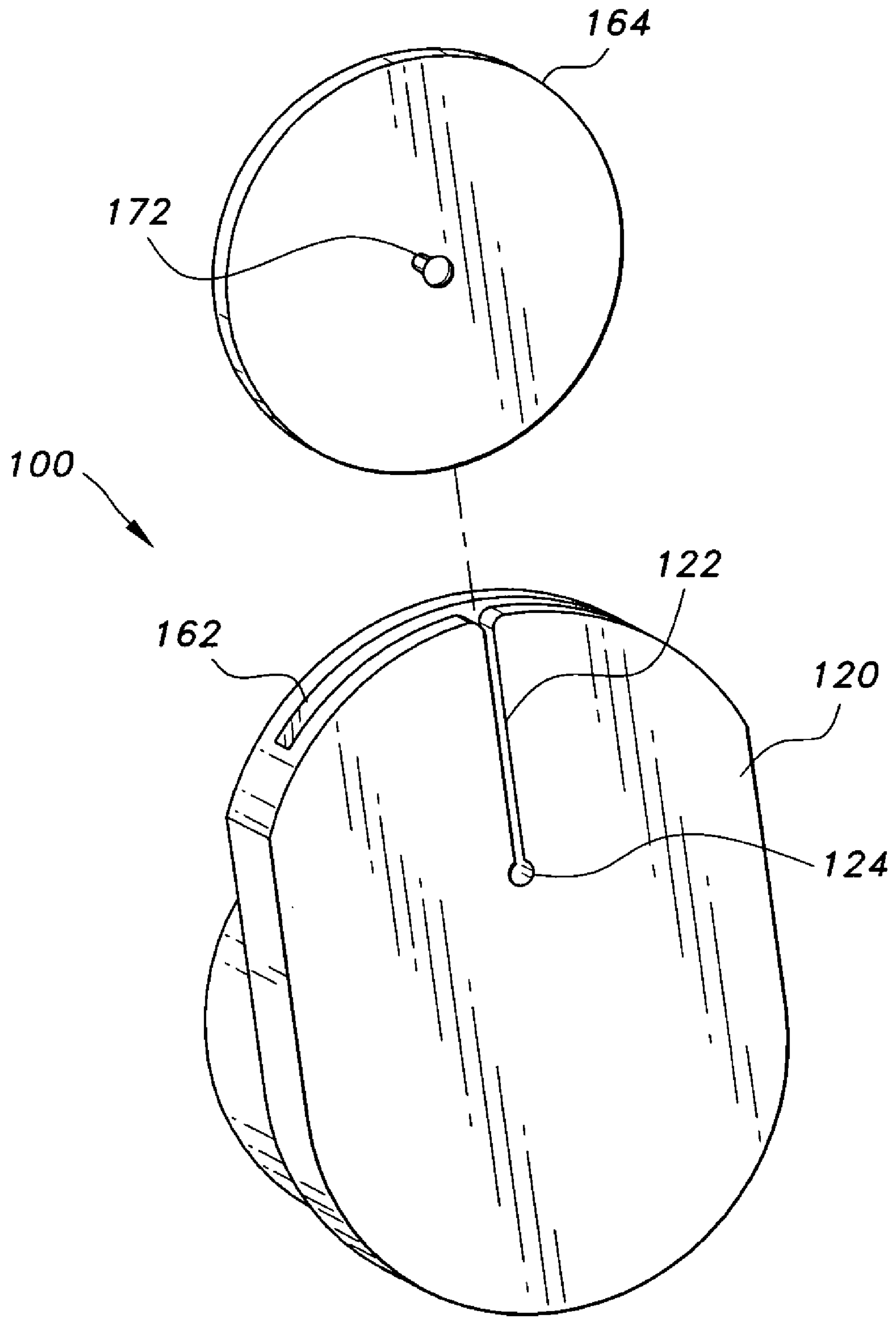
FIG. 7 is an exploded, rear perspective view of the infant eye trainer according to an additional embodiment of the present invention.

FIG. 7 depicts an additional embodiment of the infant eye trainer 100. The infant eye trainer 100 according to the present embodiment provides a safer design of the image wheel 164. In the present invention the eye trainer 100 has a wheel insertion slot 162 disposed along the top of the eye trainer 100. A knob receiving slot 122 is disposed along the rear surface 120 of the infant eye trainer 100. The infant eye trainer 100 further comprises an image wheel 164 having a wheel turning knob 172 disposed on the rear of the image wheel 164.

When the image wheel 164 is inserted into the wheel insertion slot 162 on the eye trainer 100, the wheel turning knob 172 slides down through the knob receiving slot 122. The knob receiving slot 122 provides a knob retaining portion 124 that secures the turning knob 172 in place while the image wheel 164 is inserted in the eye trainer 100. While the turning knob 172 is positioned in the knob retaining portion 124 the user of the eye trainer 100 may turn the knob 174 to rotate the image wheel 164. The wheel turning knob 174 secured to the rear of the image wheel 164 replaces the knob 66 that is releasably secured to the rear of the eye trainer 10 in the previous embodiments. The present design prevents the knob 174 from being removed by the child and swallowed, thus preventing harm to the child.

It is to be understood that the present invention is not limited to the sole embodiments described above, but encompasses any and all embodiments within the scope of the following claims.

I claim:

1. An infant eye training device, comprising:

a case having a front panel and a rear panel;

an image display device disposed in the front panel;

an insertion port defined in the case;

an image storage medium removably inserted in the insertion port, the storage medium having a plurality of images stored thereon;

an image selector for selecting an image stored on the image storage medium for display on the image display device; and a bottle mount for mounting the case on the base of a baby bottle.

2. The infant eye training device according to claim 1, wherein said bottle mount comprises a generally circular flange protruding from the front panel of said case, the flange having an inner diameter greater than the diameter of a baby bottle; and a resilient adapter ring secured around the base of a baby bottle.

3. The infant eye trainer according to claim 2, wherein said adapter ring is made from foam rubber.

4. The infant eye trainer according to claim 1, wherein said image display device comprises a liquid crystal display panel.

5. The infant eye trainer according to claim 1, wherein said image storage medium comprises an external read only memory cartridge.

6. The infant eye trainer according to claim 1, further comprising a device function control disposed on the front panel of said case.

7. The infant eye trainer according to claim 1, further comprising a speaker for generating desired sounds.

8. The infant eye trainer according to claim 1, wherein said image display device comprises a transparent viewing window.

9. The infant eye trainer according to claim 1, wherein said image storage medium comprises an image wheel having at least one translucent image.

10. The infant eye trainer according to claim 9, wherein said image selector comprises a knob positioned on the rear panel of said case, said knob being secured to an axle for engaging said image wheel, whereby turning of said knob causes said image wheel to rotate.

11. The infant eye trainer according to claim 1, further comprising a knob receiving slot disposed along the rear panel of said case.

12. The infant eye trainer according to claim 11, wherein said image selector comprises a knob secured directly to the image wheel whereby said knob is releasably received into said knob receiving slot.

13. An infant eye trainer, comprising:

a case having a front panel and a rear panel;

a transparent image display window disposed on the front panel;

an image wheel receiving slot defined on the case;

an image wheel, having at least one translucent image, releasably inserted into the image wheel receiving slot;

an image selector for selecting an image stored on the image wheel for display through the image display window; and a bottle mount for securing the case onto the base of a baby bottle.

14. The infant eye trainer according to claim 13, wherein said bottle mount comprises a generally circular flange protruding from the front panel of said case, the flange having an inner diameter greater than the diameter of a baby bottle; and a resilient adapter ring secured around the base of a baby bottle.

15. The infant eye trainer according to claim 13, wherein said adapter ring is made from foam rubber.

16. The infant eye trainer according to claim 13, further comprising a knob receiving slot disposed along the rear panel of said case.

17. The infant eye trainer according to claim 16, wherein said image selector comprises a knob secured directly to the image wheel whereby said knob is releasably received into said knob receiving slot.

* * * * *